US010743824B2

(12) United States Patent
Massengale (10) Patent No.: US 10,743,824 B2
(45) Date of Patent: Aug. 18, 2020

(54) SYSTEM AND APPARATUS FOR SURGICAL HARDWARE PLACEMENT (71) Applicant: Justin Massengale, Brookline Village, MA (US)

(72) Inventor: Justin Massengale, Brookline Village, MA (US)

(*) Notice: Subject to any disclaimer, the term of this patent is extended or adjusted under 35 U.S.C. 154(b) by 620 days.

(21) Appl. No.: 15/461,669

(22) Filed: Mar. 17, 2017

(65) Prior Publication Data

US 2017/0265910 A1 Sep. 21, 2017

Related U.S. Application Data (60) Provisional application No. 62/309,518, filed on Mar. 17, 2016.

(51) Int. Cl.
*A61B 6/12* (2006.01)
*A61B 90/00* (2016.01)

(52) U.S. Cl.
CPC ........ *A61B 6/12* (2013.01); *A61B 2090/3966* (2016.02)

(58) Field of Classification Search
CPC .................... A61B 6/12; A61B 2090/3966
USPC ...................................... 606/86 R
See application file for complete search history.

(56) References Cited

U.S. PATENT DOCUMENTS

2011/0144704 A1* 6/2011 Switzer ............... A61B 5/0064
606/86 R

* cited by examiner

*Primary Examiner* — Si Ming Ku
(74) *Attorney, Agent, or Firm* — Adler Pollock & Sheehan P.C.

(57) ABSTRACT

A system assists a physician in placing surgical hardware within a patient. The system includes a device having first and second radiodense strips which is placed over a patient. X-rays are taken of the device and patient and x-ray sheets are created. The system also includes a batch of transparency sheets. The transparency sheets can be aligned with the radiodense strips on the x-ray sheets to provide the physician with locations and positions for the placement of surgical hardware.

7 Claims, 11 Drawing Sheets

SYSTEM AND APPARATUS FOR SURGICAL HARDWARE PLACEMENT

CROSS REFERENCE TO RELATED APPLICATION

This application is a U.S. non-provisional patent application which claims priority from U.S. Provisional Application for Patent No. 62/309,518 filed Mar. 17, 2016 and U.S. which is incorporated herein by reference.

FIELD OF THE INVENTION

The subject disclosure relates to medical surgery, and more particularly to improved systems and apparatus for surgical hardware placement.

BACKGROUND OF THE INVENTION

Proper localization of anatomical landmarks is necessary for performing planned surgical procedures in the lumbar spine accurately, including confirmation of the proper vertebral levels to operate. This is typically achieved through the use and interpretation of intraoperative radiography by the surgeon. This is necessary because, in many situations, the exact locations of anatomical structure the surgeon desires to approach are not externally apparent by direct inspection of the patient's visible body surface when positioned for the operation. In such situations, radiographic images obtained with appropriate radio-opaque markers in place provide the surgeon with confirmation of the relationships of these markers to the underlying anatomical structures the surgeon desires to approach. In operations which do not involve the implantation of instrumentation hardware, one or two plain x-rays are usually sufficient to produce enough information to accurately and confidently achieve the surgical goals.

However, operations involving the placement of hardware instrumentation (e.g. pedicle screws) for lumbar spinal fusion operations, which have many steps, typically require multiple radiographic images to be performed during the operation. These radiographic images require time to perform and develop. Further, each radiograph exposes the patient to radiation, which has medical risks. This is particularly problematic in percutaneous and minimally invasive techniques for instrumentation, which are used to minimize the disruption of normal anatomical structures caused by traditional surgical exposures. The resulting limitations on visualization achievable in these procedures make reliance on radiographic guidance all the more crucial.

Customarily, intraoperative fluoroscopy is used to accommodate the much more frequent radiographic images that must be obtained and interpreted during these procedures. Fluoroscopy, however, exposes the patient as well as care providers, including the surgeon and surgical team, to much higher doses of radiation than they would otherwise receive from plain radiographs. Over a provider's career, such cumulative radiation exposure can greatly increase the risk of development of iatrogenic malignancies. Techniques to minimize the radiation exposure to the surgical team which are currently employed include radiographic shielding, as well as stereotactic guidance-based techniques which rely on registration of intraoperative radiographic anatomy, acquired fluoroscopically, with previously acquired patient images. Such techniques, however, can expose the patient to as much intraoperative radiation as a CT scan, which represents a substantial dose and would not be required were the intraoperative registration not necessary.

SUMMARY OF THE INVENTION

The subject technology overcomes the drawbacks of the prior art by providing a system and apparatus for navigating the placement of surgical hardware while minimizing the radiation exposure of patient and providers.

In some embodiments, the subject technology relates to a device for assisting in navigation during the placement of surgical hardware. The device has a first rail running parallel to a longitudinal axis. A second rail, offset from the first rail, runs parallel to the longitudinal axis. A central crossbar runs between the first rail and the second rail, the central crossbar running parallel to a transverse axis. In some embodiments, the first rail has a first track along an upper surface, the first track having a plurality of openings configured to accept at least one guide block. The second rail can also have a second track along an upper surface which has a plurality of openings configured to accept at least one guide block. The first rail sometimes has a plurality of lower slide slots configured to couple with at least one stacking support to orient the device with the respect to the ground. In some embodiments, the device has a first bubble level attached to the first rail, the first bubble level displaying indicia of whether the longitudinal axis is level to the ground. A second bubble level can be attached to the second rail which displays indicia of whether the transverse axis is level to the ground. In some embodiments, the central crossbar includes a first radiodense metal strip on an upper surface. A second radiodense metal strip can be placed on a side surface of first rail; or a side surface of the second rail. The metal strips can be substantially 50 mm in length.

In some embodiments, the subject technology relates to a system for placing surgical hardware within a patient after at least one x-ray is taken and at least one x-ray sheet is developed. The system includes a first and second radiodense strip. The system also includes a batch of transparency sheets at least some of which are operable to align, on the at least one x-ray sheet, with one of the radiodense strips to indicate at least one location for the placement of surgical hardware. In some cases, the batch of transparency sheets includes a first set of transparency sheets and a second set of transparency sheets. Both sets can include a sizing sheet with a plurality of sizing sheet lines. Each set can also include a number of subsets which each correspond to a specific magnification level.

In some embodiments, each subset of the first set includes a first subset sheet including a plurality of first sheet angled lines. Each first sheet angled line has an angle with respect to a horizontal line that differs from the angles of the other first sheet angled lines. Each subset of the first set can also include a plurality of positioning transparency sheets each having a plurality of angled lines, the angled lines on each positioning transparency sheet being at the same angle, with respect to a horizontal line on the positioning transparency sheet, as one of the angles of the first sheet angled lines. In some embodiments, each subset of the second set includes a first subset sheet depicting a plurality of first diagrams of pedicles. Each first diagram depicts one pedicle diameter and one pedicle rotation. In some cases, each subset of the second set includes a plurality of positioning transparency sheets depicting a plurality of second diagrams of pedicles, each second diagram: depicting a pedicle separation distance; depicting a position with respect to one of the radiodense strips; and corresponding to one of the first diagram pedicles.

In some embodiments, the subject technology relates to another system for placing surgical hardware within a patient after an x-ray is taken and after an x-ray sheet is developed. The system includes a batch of transparency sheets operable to align with radiodense indicia on the x-ray sheet to indicate at least one location for the placement of surgical hardware. In some cases, the radiodense indicia are created by placing at least one metal strip near the patient prior to the x-ray being taken. One or more of the metal strips can be substantially 50 mm in length.

BRIEF DESCRIPTION OF THE DRAWINGS

So that those having ordinary skill in the art to which the disclosed system pertains will more readily understand how to make and use the same, reference may be had to the following drawings.

DETAILED DESCRIPTION OF PREFERRED EMBODIMENT

The subject technology overcomes many of the prior art problems associated with the placement of surgical hardware. The advantages, and other features of the systems and methods disclosed herein, will become more readily apparent to those having ordinary skill in the art from the following detailed description of certain preferred embodiments taken in conjunction with the drawings, in which like reference numerals refer to like component parts, which set forth representative embodiments of the present invention.

The subject technology can be used with numerous and varied surgical procedures for placement of hardware within a patient. While the examples shown typically relate to the placement of a pedicle screw, one skilled in the art would understand that the subject technology can be implemented with other procedures as well. Generally, pedicle screw placement relates to the insertion of pedicle screws into a patient's vertebrate which can be attached via rods to rigidly support the patient's spine. Further, it is important to note that while specific terms such as "physician" are used throughout, these terms are merely used as an example of one type of expected user of the subject technology and is not meant to be limiting. It is expected that in some cases various medical personnel (i.e. nurses, medical residents physicians' assistants, technicians, etc.) or even non-medical personnel may accomplish some or all of the steps described herein.

Figure 1:
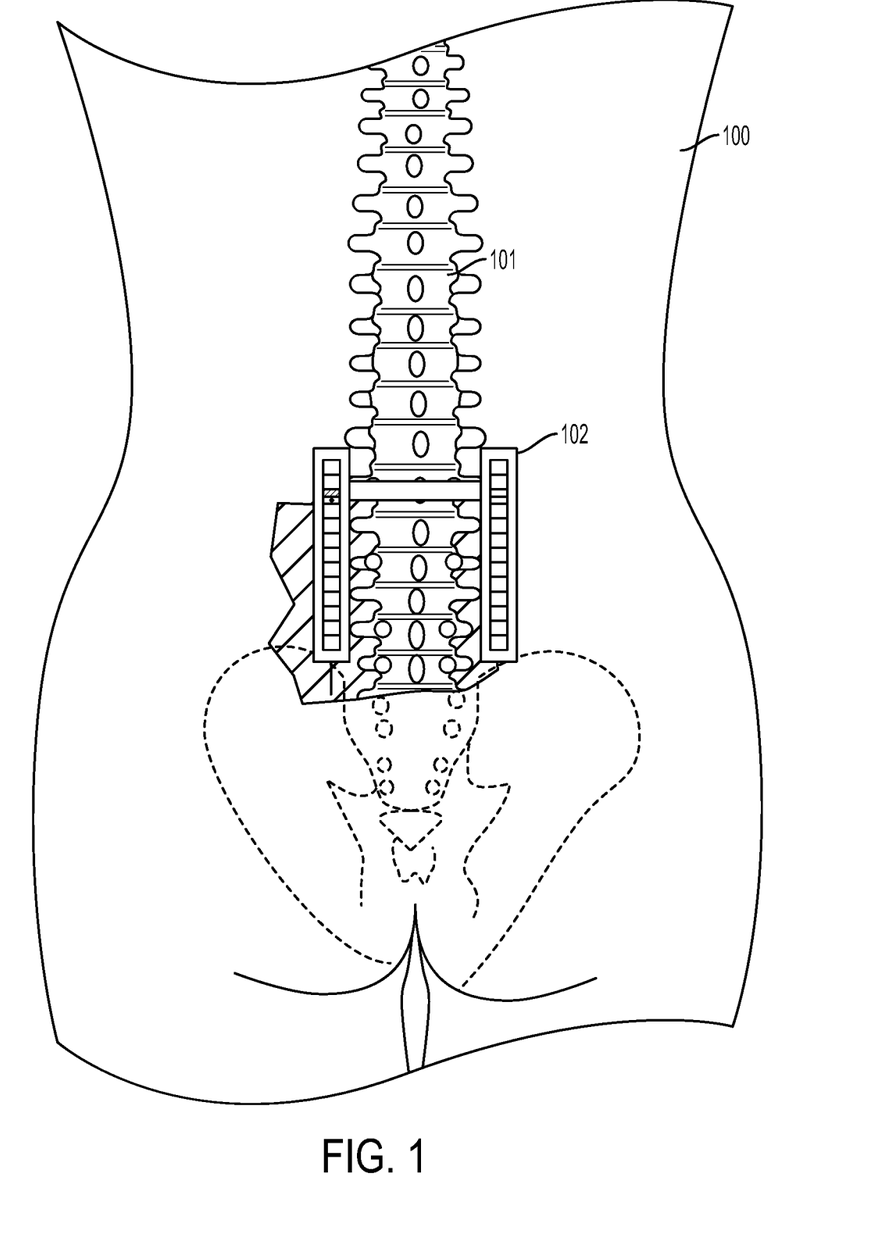
FIG. 1 is an overhead view of a device upon the back of a patient in accordance with the subject technology.

Referring now to FIG. 1, to begin the procedure for pedicle screw insertion, the patient 100 is positioned prone on an operating table (underneath the patient, not shown). A physician places a device 102 on the surface of the patient's 100 back, centered in the midline, with a location estimated to overly the vertebral levels to be instrumented. The physician palpates the skin overlying a midline spinous process (the prominence of the bony spinous process beneath the skin is typically easily palpable). After the device 102 is in place, two intraoperative x-rays are taken of the patient's 100 back—a lateral x-ray and an anterior-posterior x-ray. The device 102 works, as described in detail below, to allow a physician to place pedicle screws without taking additional X-rays.

Figure 2:
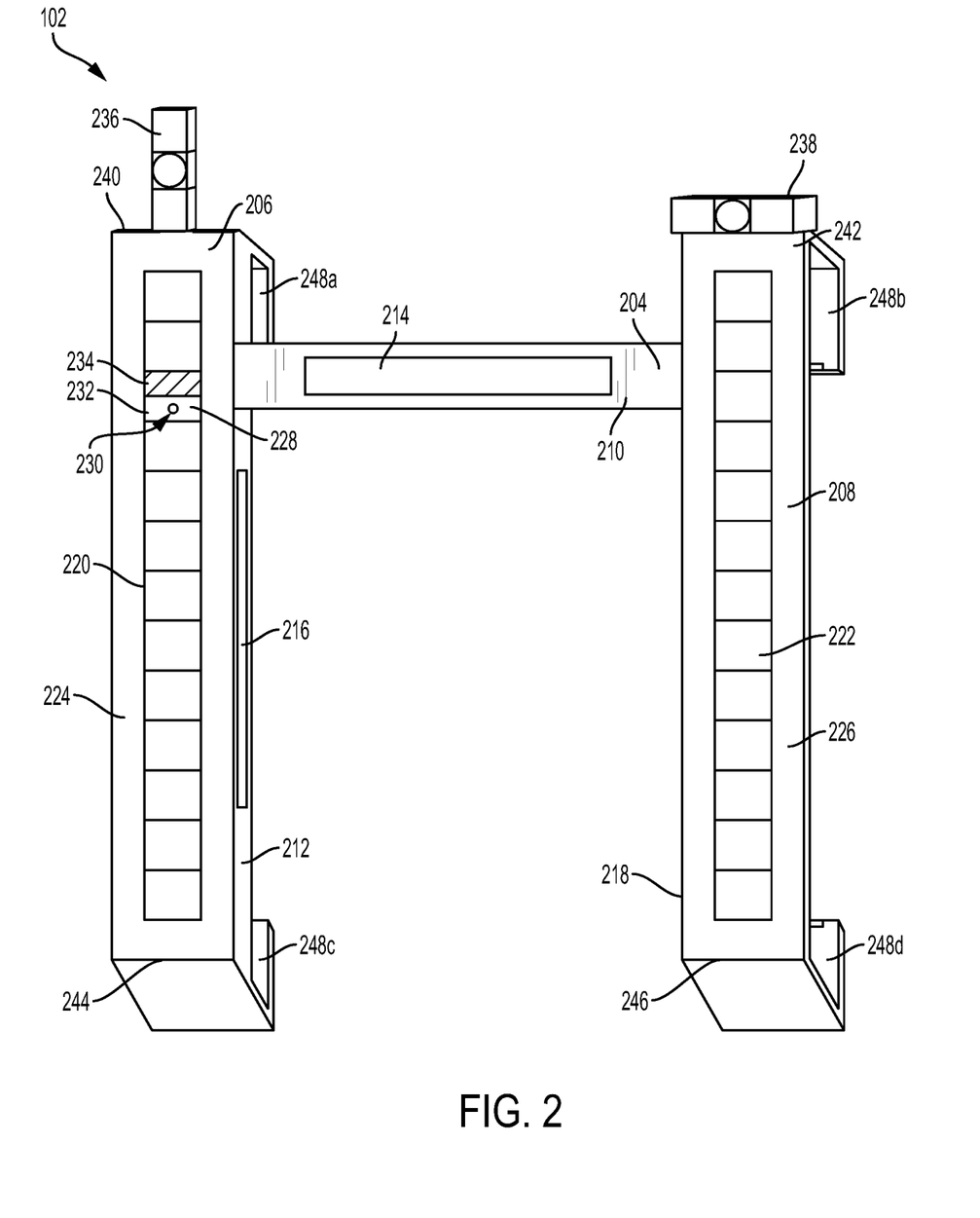
FIG. 2 is a perspective view of the device of FIG. 1.

Referring now to FIG. 2, the device 102 is shown, for better illustration, isolated from the patient's back 100. The device 102 includes a central crossbar 204 that runs between a first 206 and second rail 208. The device 102 is designed such that the rails 206, 208 can be placed on either side of, and substantially parallel to, the patient's spine 101 with the crossbar 204 running transverse to the patient's spine. The upper surface 210 of the central crossbar 204 and the inner surface 212 of the first rail 206 contain metal strips 214, 216 that are radiodense (meaning they will show up on an x-ray). Therefore when the initial intraoperative x-rays are taken after placement of the device 102 on the patient's 100 back, the metal strips 214, 216 should be visible on the x-ray sheets. Particularly, the metal strip 214 on the crossbar 204 should be visible on the anterior-posterior x-ray and the metal strip 216 on the first rail 206 should be visible on the lateral x-ray. In some embodiments, the inner surface 218 of the second rail may include a metal strip, in addition to, or as an alternative to, the metal strip 216 on the first rail 206. In some cases, the metal strips 214, 216 are exactly 50 mm in length.

The rails 206, 208 have tracks 220, 222 along the lengths of their upper surfaces 224, 226, into which guide blocks 228 can be inserted. For the sake of simplicity, only one guide block 228 is shown herein, however, multiple guide blocks are used in many embodiments. The guide blocks 228 have angled slots 230 along the outer faces 232 which provide guidance for directing Jamshidi needles (not shown herein) into the pedicles of the patient 100. One or more spacing blocks 234, which lack slots, can also be inserted within the tracks 220, 222. The spacing blocks 234 are used to space the guide blocks 232 correctly within the device 102. For example, the spacing blocks 234 could be used to provide a fixed distance between two guide blocks 228. Alternatively, a spacing block 234 could be used to hold a guide block 228 at a fixed location within one of the tracks 220, 222, as shown in FIG. 2. Multiple spacing blocks 232 are used in many embodiments, the spacing blocks 232 having different lengths to provide different spacing options. The length of each spacing block 232, as well as the order of inserting the spacing blocks 232 into the rails 206, 208, is determined by the physician's discretion after a review of the patient's 100 intraoperative x-ray images.

Still referring to FIG. 2, the device 102 contains two built in bubble levels 236, 238. The first bubble level 236 is positioned on the first end 240 of the first rail 206 and is oriented parallel to the first rail 206. The second bubble level 238 is positioned on the first end 242 of the second rail 208 and is oriented perpendicular to the rail 208. Together, movement of the air bubble within the mostly liquid filled bubble levels 236, 238 allows the physician to see if the device 102 is not properly leveled. Both ends of each rail 240, 242, 244, 246 also have slots 248a-248d on their undersides. The underside slots 248a-248d are meant to accept stacking foot-like supports (not shown herein) which are inserted into the slots 248a-248d. If the device 102 is not properly level, these supports can be inserted into the slot 248a-248d as needed to properly level the device 102 with respect to the ground. Alternatively, or additionally, supports can be affixed to the underside slots 248a-248d to orient the device 102 such that it appears perfectly flat and/or level on any x-rays taken (i.e. so that the device 102 runs parallel to the x-ray machine). Therefore even though the patient's body 100 and spine 101 might not be exactly level, the device 102 can be situated in a substantially level position.

Once the device 102 is level and properly positioned on the patient's 100 back, the device 102 can be used for the placement of surgical hardware. For example, in some cases the device 102 can be used for the placement of anchoring Jamshidi needles. To do so, multiple guide blocks 228 and spacing blocks 234 can be placed within the tracks 220, 222, as discussed above. The physician then prepares the skin at the planned insertion point by scrubbing the skin with iodine. The Jamshidi needle is then worked through one of the guide blocks 228. The guide block 228 is held in a desired position within one of the tracks 220, 222 by spacing blocks 234. Further, the guide block 228 has an angled opening 230 to direct the Jamshidi needle into the patient 100 at a desired angle. The physician presses the Jamshidi needle through the guiding block 228 until it impacts the skin and closes hinged grabbing tongs on the Jamshidi needle to hold the skin in a straight, upright position. The physician then advances the Jamshidi needle through the patient's 100 skin with gentle downward pressure, until bone is encountered. Using a mallet, the physician then impacts the needle into the bone about 5 mm.

In some cases, the device 102 can used in conjunction with transparency sheets as part of a system for identifying the correct positions and angles of insertion for Jamshidi needles, or other surgical hardware. For example, referring now to FIGS. 3-11, a system of using the device 102 in conjunction with a number of transparency sheets to effectuate proper pedicle screw placement is described. As used herein, the term "transparency sheet" (or sometimes just "sheet") refers to a substantially transparent sheet with a number of markings on it. Being mostly transparent (or see-through), the transparency sheets can be placed over other sheets or images (i.e. x-rays) while still allowing the user to see the majority of the underlying sheet or image through the transparency. The markings on the transparency sheet, which are more opaque than the sheet itself, can then be positioned to measure, identify, align with, or otherwise denote a position with respect to the underlying x-ray sheet or image. The physician can then rely on the positioning shown by a transparency sheet with respect to the underlying x-ray sheet or image in order to determine a correct location or position for the placement of surgical hardware. In this way, and as discussed below in more detail, one or more transparency sheets can help the surgeon place surgical hardware without the need for an excessive amount of x-rays (i.e. sometimes only 2) and without exposing medical staff or the patient 100 to excessive radiation. Various amounts of transparency sheets, or sets of transparency sheets, can be used in different embodiments.

Figure 3:
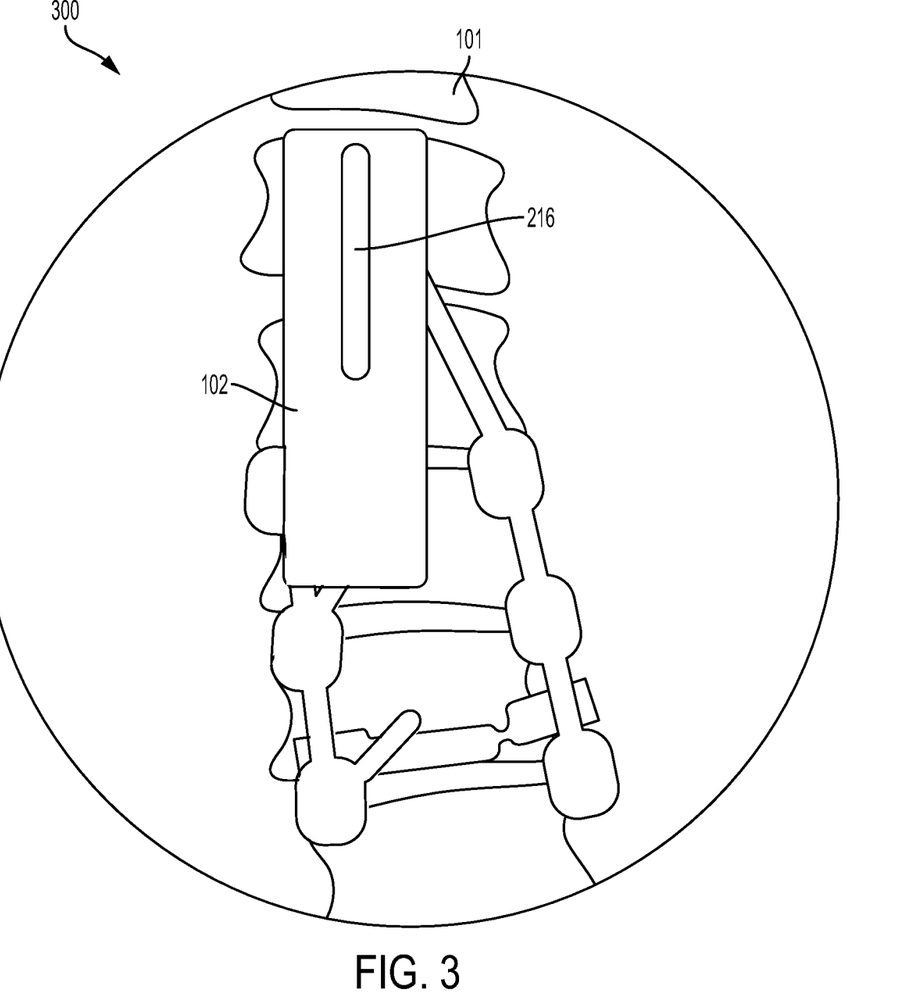
FIG. 3 is an overhead view of a lateral x-ray of a patient's back and the device in accordance with the subject technology.

For example, referring now to FIG. 3, an x-ray sheet showing a lateral x-ray of the spine 101 with the device 102 in place, is shown generally at 300. On the x-ray sheet 300, the device 102 as a whole appears as a rectangular radiolucent (transparent on an x-ray) shadow. Since the x-ray is taken from the side of the patient 100, the metal strip 216 which runs along the first rail 206 is visible as a radiodense longitudinal bar.

Figure 4:
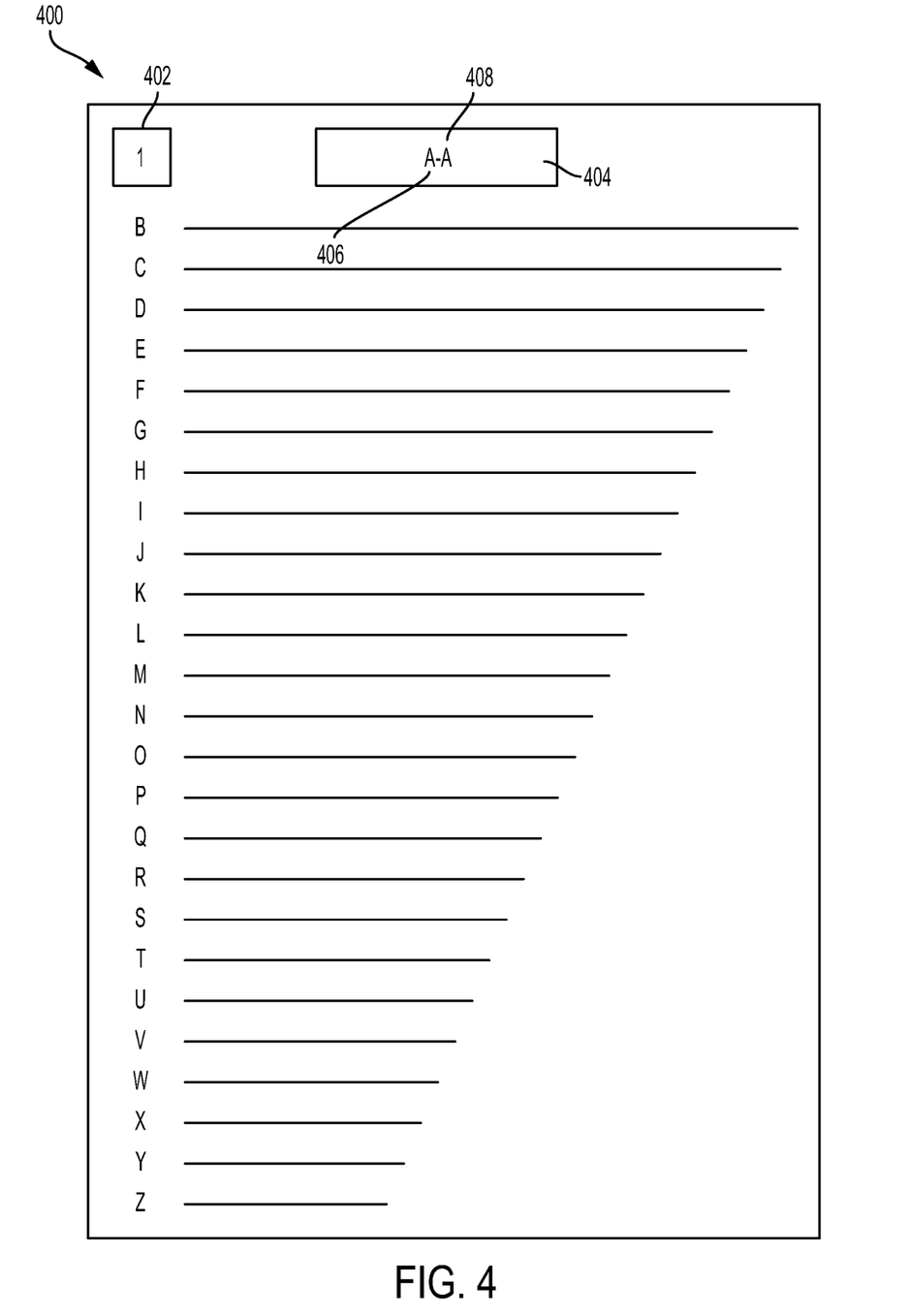
FIG. 4 is an overhead view of a sample first set sizing transparency sheet in accordance with the subject technology.
Figure 5:
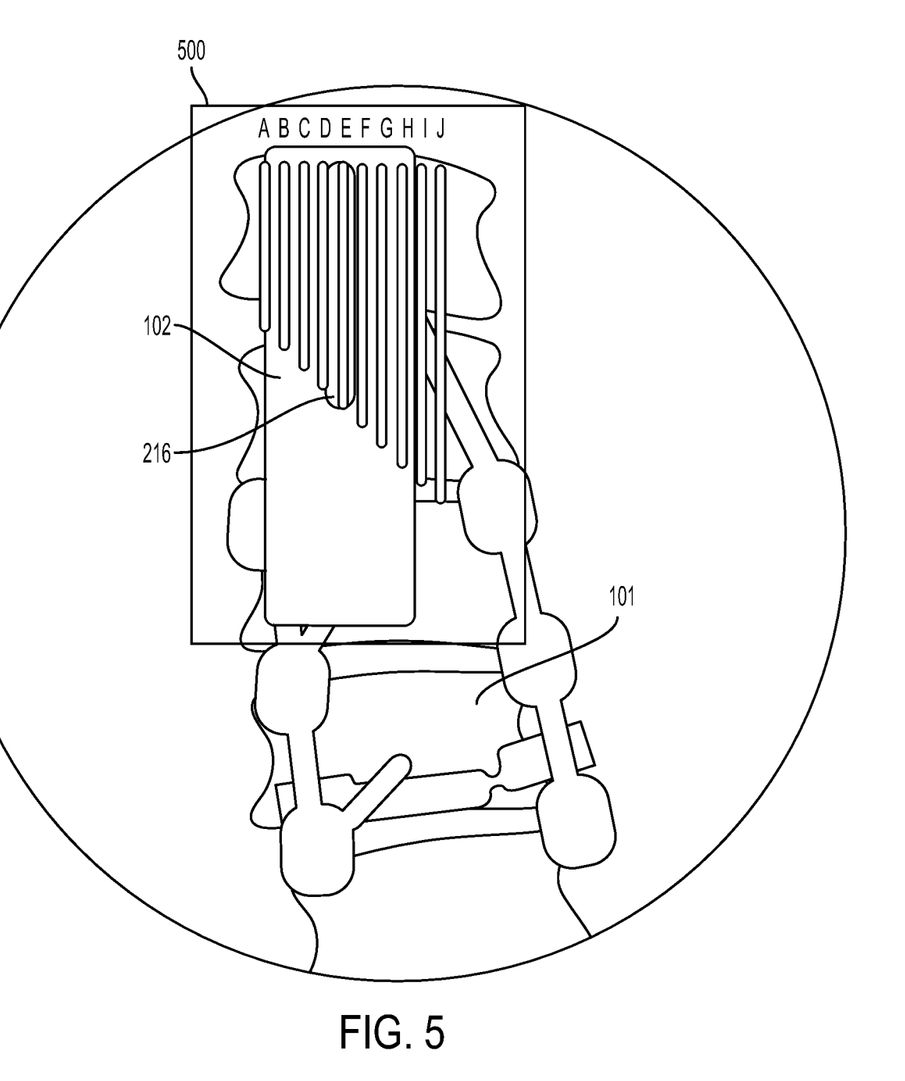
FIG. 5 is an overhead view of a sample first set sizing transparency sheet placed over the x-ray of FIG. 3.

Referring now to FIG. 4, a sizing sheet 400 is shown from a sample embodiment of a batch of transparency sheets which includes two sets. As shown, the sizing sheet 400 has indicia of the set number 402. Normally, the label 404 on a transparency sheet includes a first indicia of a subset 406 and indicia denoting a specific sheet within that subset 408. However, in the example shown, the sizing sheet is marked differently than the other sheets and is instead marked "A-A" to denote that it is the sizing sheet. The sizing sheet 400 indicates 25 different subsets ("B-Z"), each associated with a line of a different length which are used to select a subset. Each subset contains an additional number of transparency sheets (in some cases, 26). For example, the first transparency sheet of subset B is labeled "B-A", the second "B-B", the third "B-C", and so on. The first transparency sheet of each subset in the first set shows diagrams representing the most commonly encountered sagittal angles of the vertebral endplates of the lumbar spine, and are used to gather data about the sagittal angle of the vertebral endplates from the lateral intraoperative x-ray images taken during the procedure, as described more fully herein.

It should be noted that the transparency sheet batch which is shown and described herein has been found to be advantageous for some applications. However, the positioning, content, and arrangement of the transparency sheets shown is subject to change depending on the discretion of the medical provider and the type of application. Similarly, the number of transparency sheets and numbers of sets of transparency sheets shown in the batch is shown to provide an example and is not meant to be all inclusive.

Still referring to FIG. 4, in the example shown, the sizing sheet 400 is the first sheet of the first set of transparency sheets. The sizing sheet 400 shows lines of varying lengths, labeled "B"-"Z", each corresponding to a subset within the first set, which are measured against the length of the metal strip 216 as seen in one of the intraoperative x-rays (in this case the lateral x-ray). This can be done by placing the sizing sheet 400 directly over the lateral X-ray sheet depicting the lateral intraoperative x-ray described above. When a match is found (or the line most closely matching the length of the metal strip is determined) the label of the matching line is used to determine the proper subset, which is then used to plan incision positions and screw insertion angles. For example, referring to FIG. 5, a sizing sheet 500 is shown, positioned over the x-ray of FIG. 3. Note that in this example, for better illustration, the sizing sheet 500 is shown with only lines for "B"-"K" being shown. As can be seen, in the example shown, the metal strip 216 most closely corresponds with line "E", and therefore this signals that subset "E" will be used. Therefore, the transparency sheets that will be used in the example procedure will all start with the letter "E" to denote their subset.

Notably, the different subsets merely indicate a different degree of magnification. Across the various subsets, the transparency sheets having similar last markings (or indicia) are similar, except for slight differences in magnification. For example, each transparency sheet in subset B is identical to the corresponding transparency sheet in subset C, other than a very small difference in magnification of the items on the sheet compared to the corresponding sheet in other subsets. So, for example, everything on sheet "C-E" is identical to everything on sheet "B-E", but a little smaller. The percent reduction factor in the size of the items on each successive subset is equal to the percentage difference between the size of the horizontal lines on the sizing sheet "A-A" (i.e. the difference in magnification between "B-E" and "C-E" would be proportional to the difference between lines "B" and "C" on sheet "A-A"). This enables data to be gathered about distances on the intraoperative x-ray images when the size of objects on the displayed x-rays is unpredictable from patient to patient, and is dependent on acquisition factors such as the distance of the film from the patient as well as display factors such as the size and resolution of the display monitor.

Figure 6:
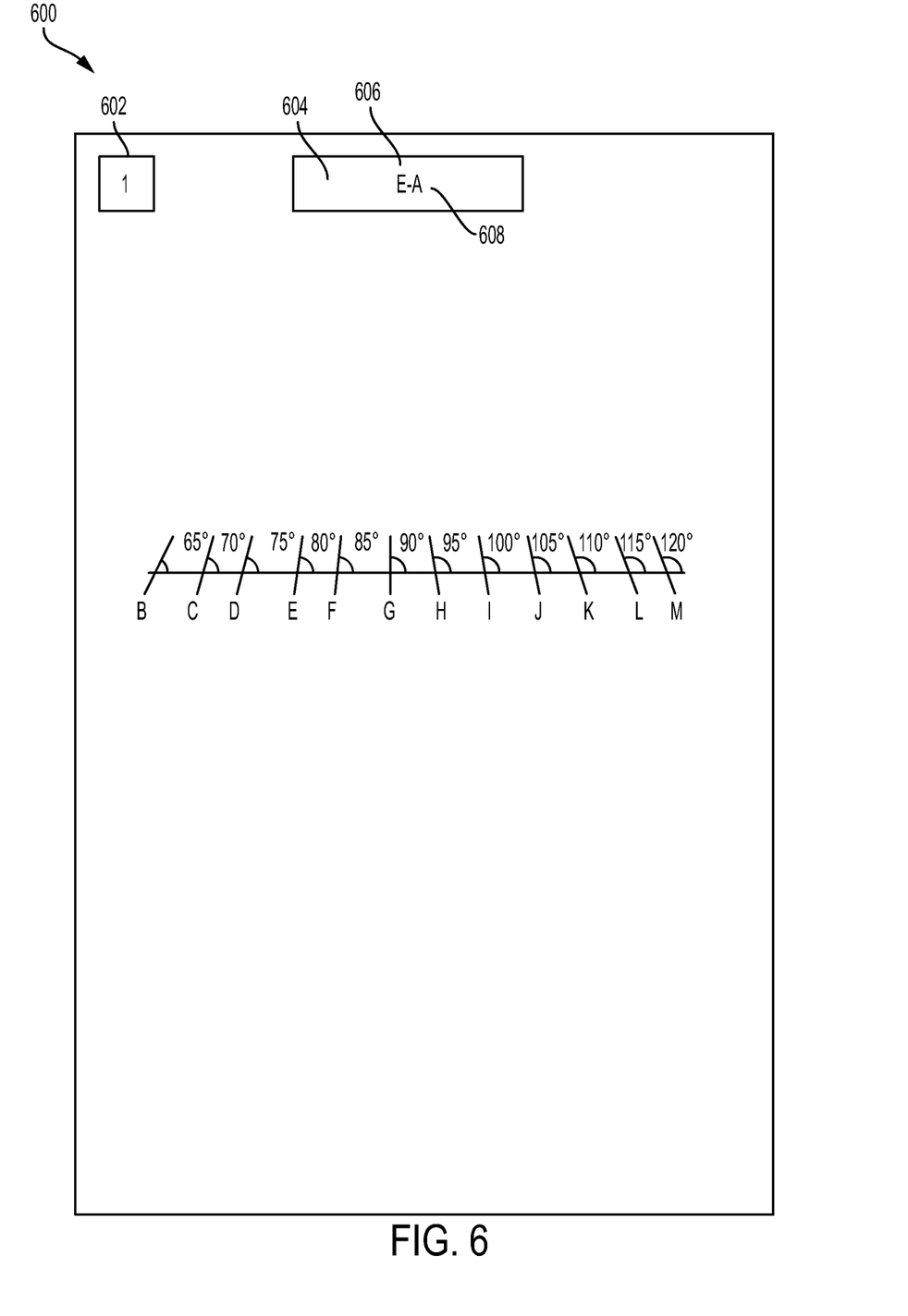
FIG. 6 is an overhead view of a sample first set, first subset transparency sheet in accordance with the subject technology.

Referring now to FIG. 6, and continuing with the example shown above, the first transparency sheet 600 of subset E is a subset sizing sheet labeled "E-A." As mentioned above, the transparency sheet 600 has an indicia of its set 602, as well as a label 604 with a first indicia of its subset 606 and a second indicia 608 of which sheet it is within that subset. Notably, a second indicia 608 of "A" indicates that it is a subset sizing sheet. All other sheets within the subset (in this case, those having second indicia 608 of "B"-"M") are "positioning sheets" which show final locations and orientations for surgical hardware placement. As mentioned above, the sheets within subset "E" each show a horizontal line of the same size as line "E" from sizing sheet "A-A". Sheet "E-A" contains a horizontal line crossed by 12 additional lines which make angles of 65, 70, 75, 80, 85, 90, 95, 100, 105, 110, 115, and 120 degrees with the horizontal line and are each labeled with a letter, "B" through "M", respectively.

Figure 7:
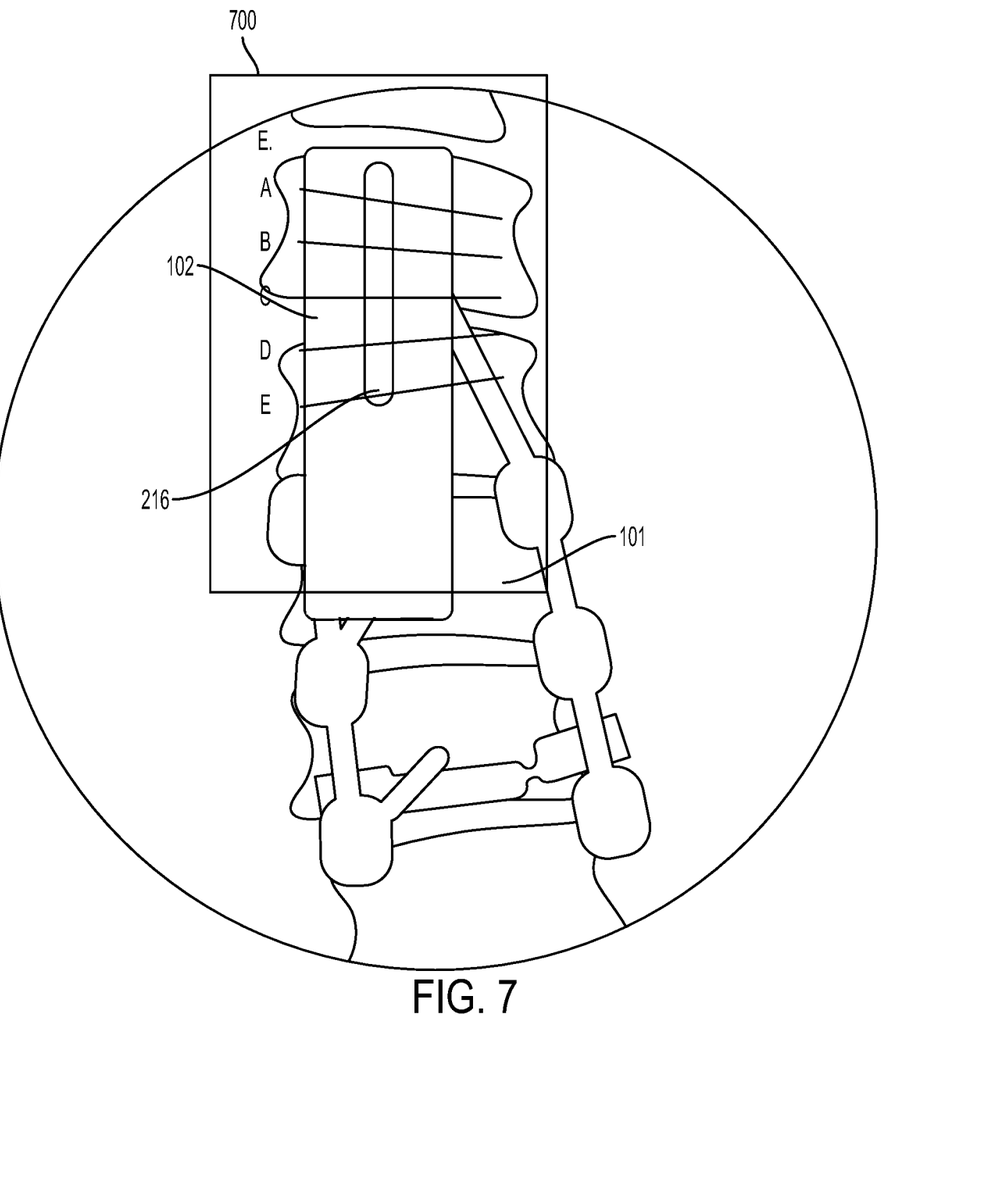
FIG. 7 is an overhead view of a sample first set, first subset transparency sheet placed over the x-ray of FIG. 3.

Referring to FIG. 7 an example of a first transparency sheet 700 of a subset is shown being placed over an x-ray sheet to determine a hardware placement angle is shown. The transparency sheet shown in FIG. 7 is similar to the transparency sheet 600 (FIG. 6) as discussed above, except that is simplified for illustrative purposes and oriented somewhat differently. When the sheet 700 is placed over an x-ray, the physician can determine the desired angle for hardware placement that is the best match given the positioning of the patient's body parts (i.e. the shape of their spine 101). When the desired angle is selected, the transparency sheet is selected within subset "E" that has a final marking which corresponds with the marking of the next to the line of the desired angle.

Figure 8:
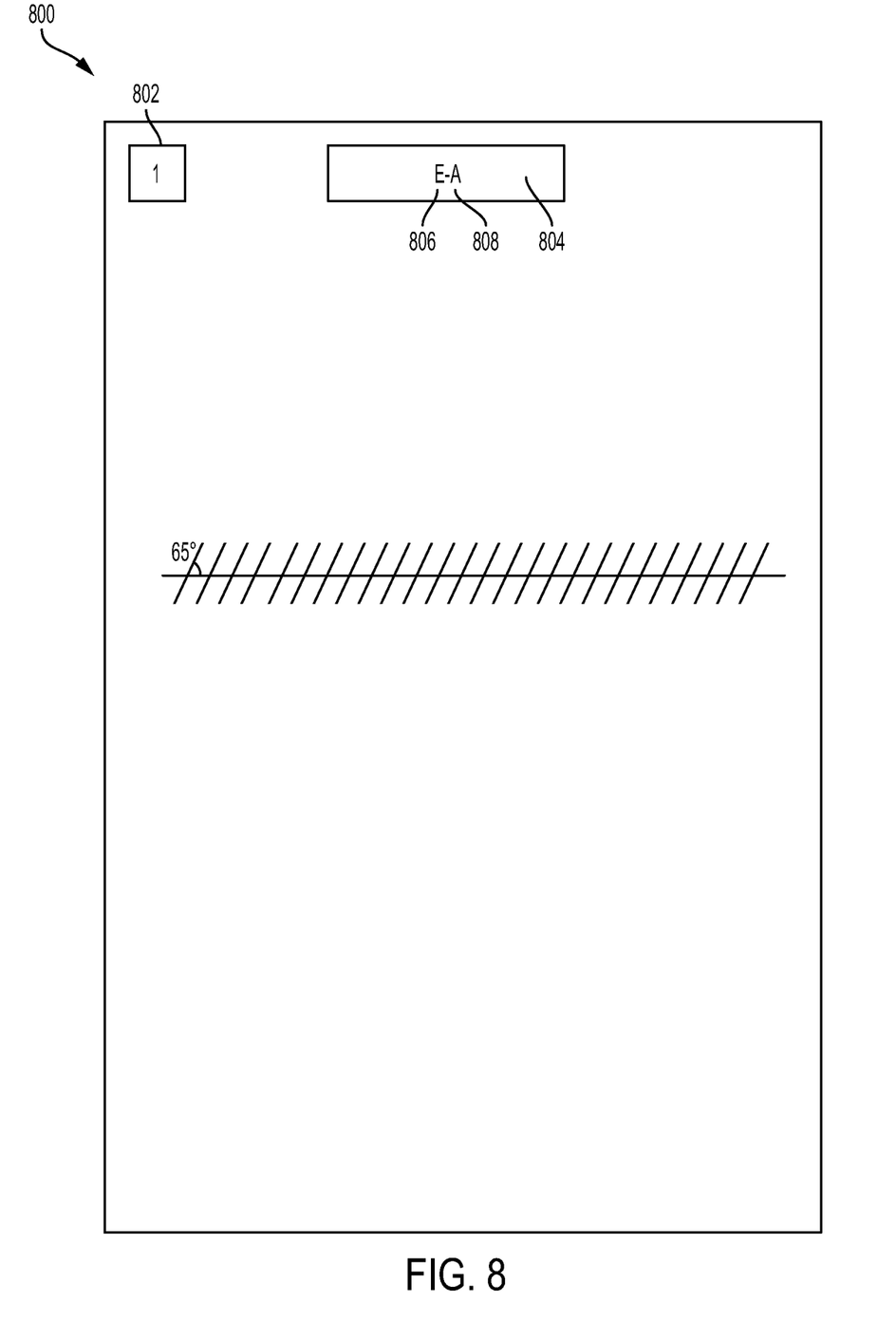
FIG. 8 is an overhead view of another sample first set transparency sheet in accordance with the subject technology.

For example, referring to FIG. 8, transparency sheet "E-B" is shown, generally at 800, which corresponds with a selection of a 65 degree angle, associated with the marking "B", from sheet "E-A" (see FIG. 6). As with the other transparency sheets, the sheet 800 has an indicia of set 802, and a label 804 with indicia of subset 806 and sheet within that subset 808. As with all sheets within subset "E", the sheet 800 contains a horizontal line of the same length as the line labeled "E" on sheet "A-A" (400). Similarly, the sheet 800 contains a total of 25 additional parallel lines which are identical in angulation with that labeled "B" on sheet "E-A" (600), but are positioned on the sheet 800 with distances 5 mm apart. The other transparency sheets within subset "E" function similarly to sheet "E-B" (800), as discussed above. For example, sheet "E-C" contains a horizontal line of the same length as the line labeled "E" on sheet "A-A" (400), and a total of 25 additional parallel lines which are identical in angulation with that labeled "C" on sheet "E-A" (600), positioned 5 mm apart. These lines help a physician determine a final position and/or orientation for the placement of surgical hardware. Therefore the sheet 800 shown, as well as all other sheets within subset "E" other than the initial sheet "E-A" (600) serve as positioning sheets.

Likewise, these similarities hold true across different subsets, the subsets differing only in their size. For example, sheets denoted "F-B" through "F-M" all have a horizontal line of the same length as the line labeled "F" on sheet "A-A" (400), but parallel lines which are angulated according to the respective marking on sheet "F-A" that corresponds to the final marking of that label for that sheet (i.e. "F-C" would have parallel lines of the same angle as line "C" on sheet "F-A"). All total, there are 300 of such positioning transparency sheets in the first set, representing a combination of 25 possible horizontal line lengths plus 12 possible angles of the angled lines.

Figure 9:
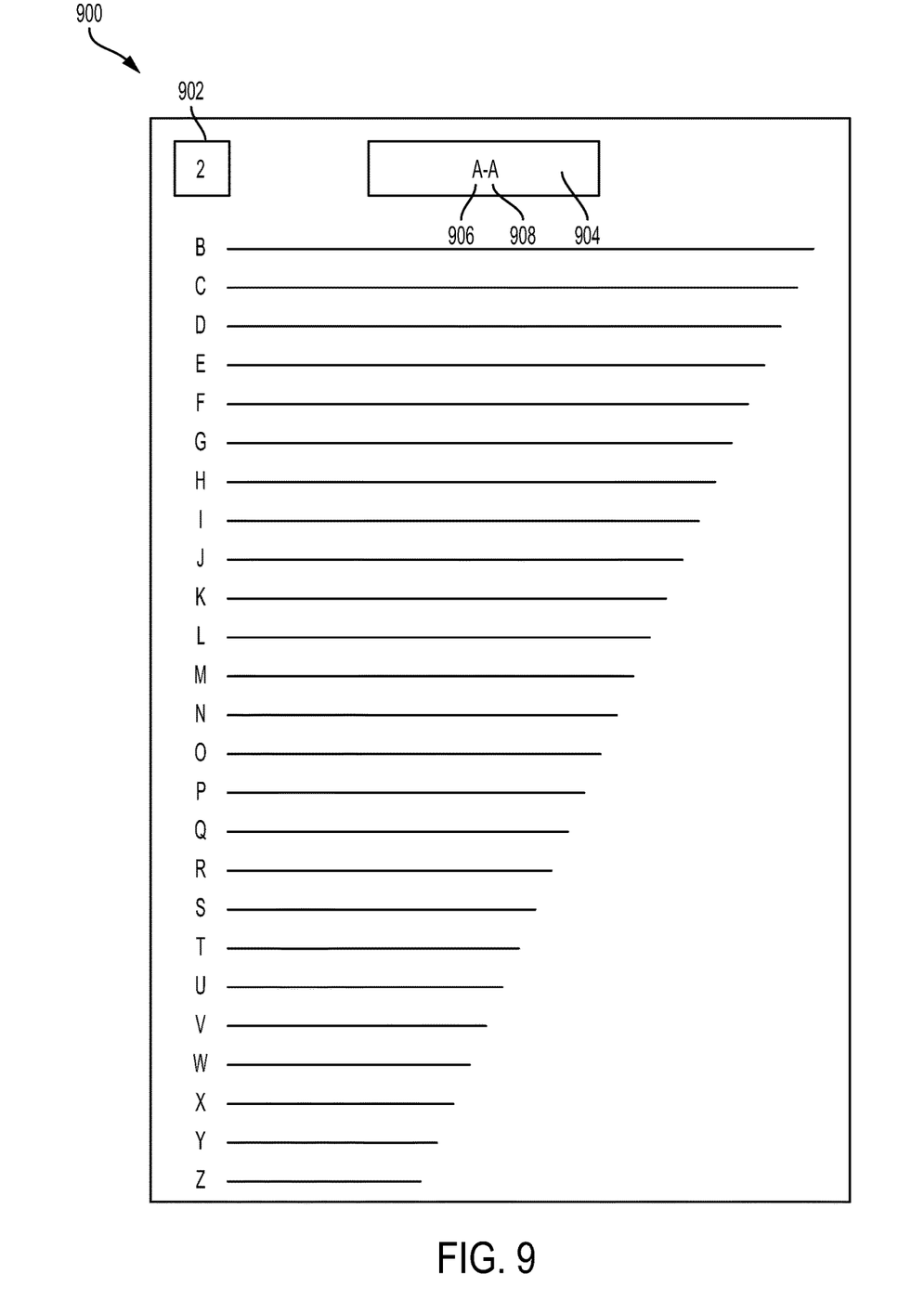
FIG. 9 is an overhead view of a sample second set sizing transparency sheet in accordance with the subject technology.
Figure 10:
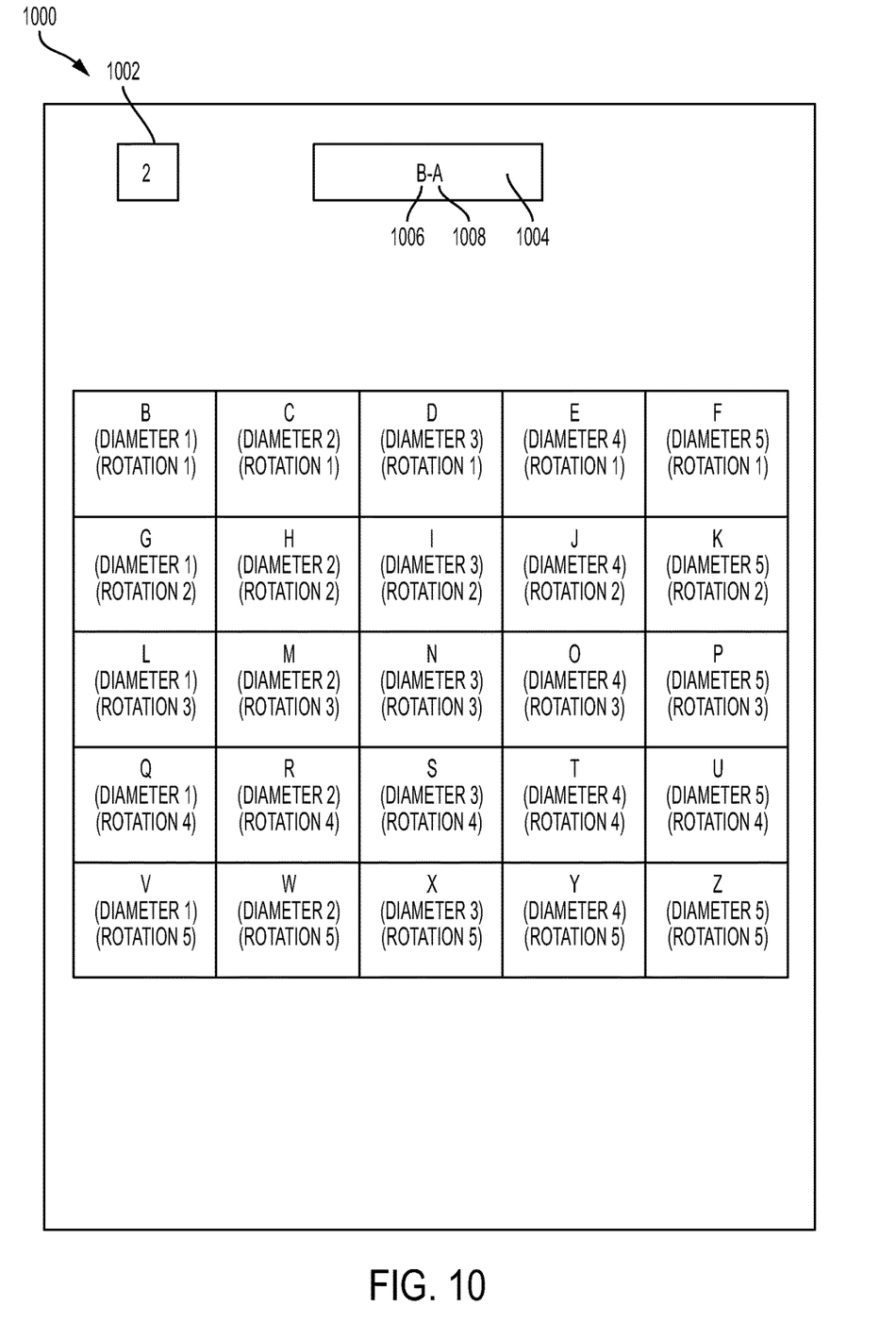
FIG. 10 is an overhead view of a sample second set, second subset transparency sheet in accordance with the subject technology.
Figure 11:
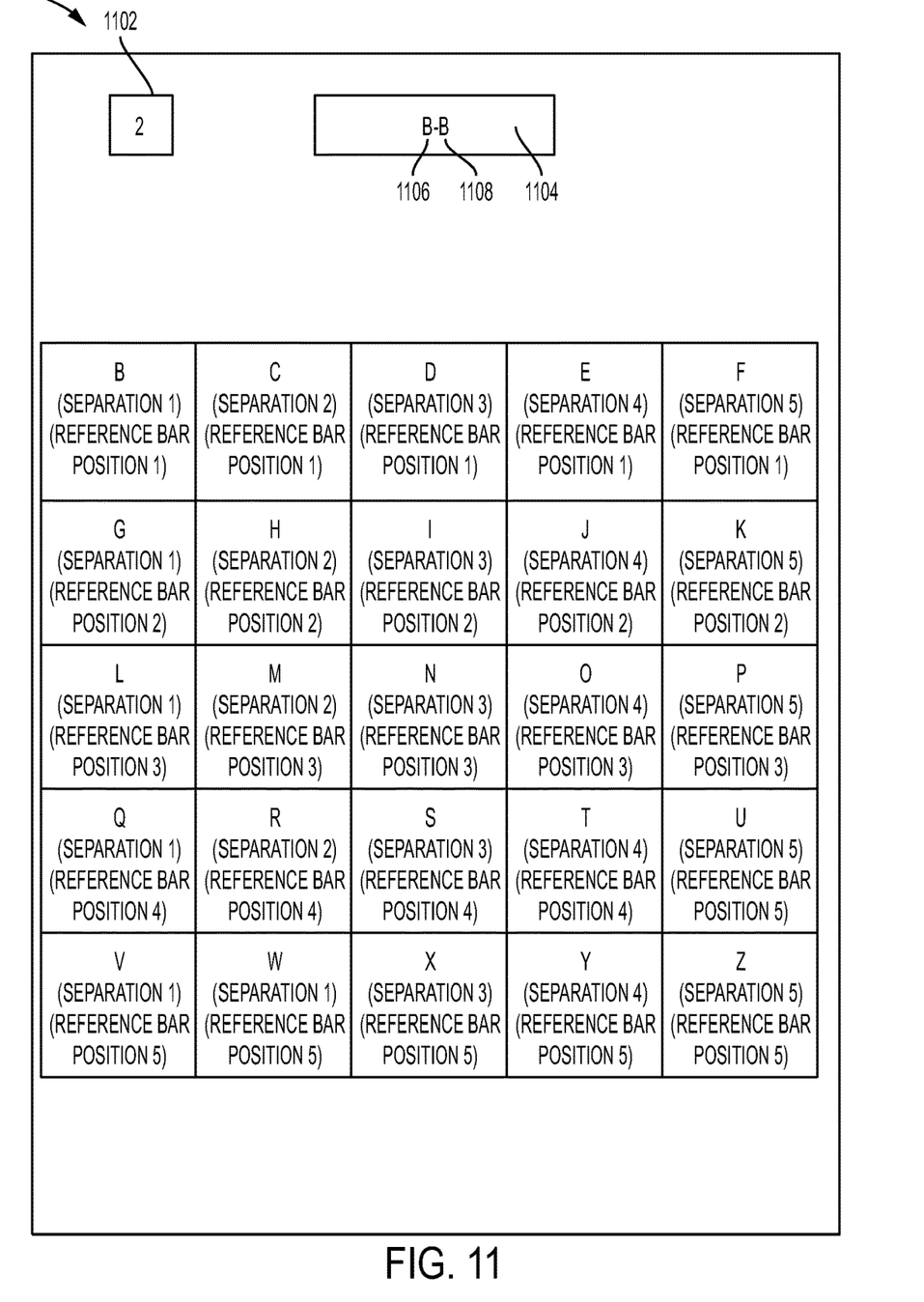
FIG. 11 is an overhead view of another sample second set transparency sheet in accordance with the subject technology.

Referring now to FIGS. 9-11, various example transparency sheets from the second set of transparency sheets for the sample batch are shown. The second set of transparency sheets, other than the sizing sheet, generally show diagrams of the appearance of pedicles in the anterior-posterior x-ray dimension. The diagrams are used for gathering and interpreting data obtained from the anterior-posterior intraoperative x-ray images. As with the first set, the second set of transparency sheets are divided up into 26 subsets (or a first sizing sheet labeled "A-A" and 25 subsets) which are referred to by letters.

Referring now to FIG. 9, the sizing sheet 900 of the second set of transparency sheets is shown. As with the first set, the sizing sheet 900 of the second set contains 25 horizontal lines of different lengths corresponding to the labels "B" through "Z". However, while lines from the sizing sheet of the first set correspond to the metal strip shown on the lateral x-ray, the lines from the sizing sheet of the second set are used to align with the metal strip along the central crossbar which is visible on the anterior-posterior x-ray. Similar to the first set, there are an additional 25 subsets of transparency sheets marked "B" through "Z" which correspond to the lines shown on the sizing sheet. The sizing sheet 900 includes indicia 902 denoting that it is part of the second set, as well as a label 904 indicating that it is the sizing sheet (i.e. "A-A") of the second set.

Referring now to FIG. 10, an example subset sheet from the second set labeled "B-A" is shown generally at 1000. The sheet 1000 includes indicia 1002 that it is part of the second set, and a label with indicia 1006 that it is in subset "B" and indicia 1008 that it is the first sheet within that subset. In the second set, the first sheet of each subset ("B-A", "C-A", etc.) contains 25 diagrams depicting the appearance of pedicles and spinous processes on anterior-posterior intraoperative x-ray images. As with the first set, the subsets refer to different magnificent levels which correspond with the lengths of the lines on the sizing sheet 900. Notably, in the example shown, the diagrams themselves have been omitted in lieu of descriptions of the way in which the diagrams differ from one another. However, one skilled in the art would understand that in practice, actual diagrams of pedicles and spinous processes on anterior-posterior intraoperative x-ray images would be displayed in the diagram boxes. The pedicles depicted in these diagrams have slightly different diameters and are shown in configurations representing different vertebral body rotations. In all, diagrams on the first sheet of each subset depict a combination of 5 different pedicle diameters and 5 different pedicle rotations for a total of 25 unique diagrams, each labeled with a letter ("B" through "Z"). When a proper diameter and rotation is selected, in accordance with the discretion of the physician, the physician can then move to the proper transparency sheet within that subset. The diagrams on the other transparency sheets of each of these subsets ("B-B", for example) show anterior-posterior views of the pedicles with the same diameter and rotation as one of the combinations on the first sheet of their subset, but are configured so as to depict what the pedicle would look like with different pedicle separation distances and different positions of the metal strip 214 on the device 102 with respect to the pedicles.

For example, turning to FIG. 11, a sample transparency sheet 1100 is shown for the transparency sheet "B-B". As explained above, the label 1104 of "B-B" indicates that the sheet 1100 is in subset "B" (as per the first indicia on the label 1106) and is sheet "B" within that subset (as per the second indicia on the label 1108). Thus, "B-B" corresponds to selection "B" from sheet "B-A". Therefore all the diagrams shown on sheet "B-B" (1100) depict a pedicle diameter and rotation in accordance with those shown in box "B" of sheet "B-A" (1000). The diagrams shown on transparency sheet "B-B" (1100) further show a series of diagrams with that pedicle diameter and rotation, that having varying pedicle separation and reference bar (i.e. metal strip 214) positions. In all, 5 different pedicle separation distances and 5 different metal bar positions are shown for a total of 25 unique combinations. In this way, the sheets within each subset after "A" (sheets "B"-"Z") are positioning sheets used for the final positioning and orientation of surgical hardware by the surgeon.

Similarly, the other 25 subsets within the second set ("C", "D", "E", etc.) all similarly show 5 different diameters and 5 different rotations on the initial sheet of the subset ("C-A", "D-A", "E-A", etc.). Each of these subsets also contain 25 other sheets within the subset, as described with respect to subset "B", which show 25 diagrams depicting 5 different pedicle separation distances and 5 different reference bar positions. Thus in overview, within the second set, there are 25 metal stripe lengths corresponding to subsets, each subset having 25 diameter and rotation orientations which correspond to a transparency sheet which shows 25 different separation distances and reference bar positions. Therefore there are 625 different positioning transparency sheets within the second set. However, as mentioned above, it should be noted that this particular transparency sheet 1100 is one embodiment of the subject technology and different transparency sheets may be used in other embodiments. Using these diagrams, the physician can select the combination of these imaging characteristics that is most similar to the actual appearance of the patient's anatomy. In this way, the transparency sheets provide data for the selection of screw trajectories and sizes which are most appropriate for the patient's anatomy, as described in more detail below.

For example, after the lateral and posterior-anterior x-rays are taken, the lateral x-ray is placed on an x-ray viewing terminal. As discussed above, the x-ray will display a radiodense strip 214, 216 from the device 102 (FIG. 3). The physician holds up the first transparency sheet from the first set (the sizing sheet, i.e. see FIG. 4) to the screen of the terminal. The physician then matches a line from the sizing sheet which is most similar in length to the radiodense strip on the x-ray (i.e. see FIG. 5), noting the letter corresponding to that line. Then, the physician takes the transparency sizing sheet down from the screen and selects the subset which has the letter corresponding with the line that most closely matched the radiodense strip. For example, if the bar labeled "G" on transparency "A-A" was the most similar in length to that of the horizontal bar on the radiograph, the next transparency used would be "G-A". One of the angled crossing lines transparency sheet "G-A", representing the range of most likely angles of the vertebral endplates in the lumbar spine with respect to the horizontal reference bar on the device 102 (i.e. the metal strip 216) as visible on a lateral radiograph, will best match the angle of the endplate of the vertebral body on the patient's lateral radiograph which the user intends to actually instrument with a pedicle screw. The letter corresponding to that best match angle is noted, and the transparency letter within that subset that shares the appropriate angle designation is selected. For example, where "G-A" is the designation of the sheet currently on the display screen ("G-A" being the first sheet of subset "G"), if the vertebral level for which the screw information is currently being planned is L4, and the line labeled "E" on sheet "G-A" is the line which most closely approximates the radiographic angle of the upper endplate of the L4 vertebra with respect to the horizontal reference line, then the transparency "G-E" should be the next transparency sheet selected. On sheet "G-E", the line with a position and/or orientation most similar to the appropriate location for a lumbar pedicle screw in the level of interest is selected and the letter designating that line is noted.

Referring back to FIG. 2, and continuing with this example, if the line labeled "K" on the transparency sheet "G-E" is the line which is most closely overlying the position where a pedicle screw in the vertebral body of interest would be placed, then the combination of the horizontal bar length "G" with the angle "E" and the angled line position "K" are the parameters which are used to inform the user of how to select correct spacing and guide blocks 234, 228. For example, the parameters can be used to identify the angles of the slots 230 within the guide blocks 228 to be used. Further, the parameters can identify the dimensions of guide blocks 228 and spacing blocks 230 to be placed within the tracks 220, 222 in order to guide Jamshidi needles, subsequently introduced screws, or other surgical hardware into the final desired position. In this way, sheet "G-E" serves as a positioning sheet for the placement of surgical hardware.

It will be appreciated by those of ordinary skill in the pertinent art that the functions of several elements may, in alternative embodiments, be carried out by fewer elements, or a single element. All processes shown and described herein, in different embodiments, may be carried out by executing the steps in a different order, or by omitting a step or adding additional steps.

While the subject technology has been described with respect to preferred embodiments, those skilled in the art will readily appreciate that various changes and/or modifications can be made to the subject technology without departing from the spirit or scope of the subject technology. For example, each claim may depend from any or all claims in a multiple dependent manner even though such has not been originally claimed.

The invention claimed is:

1. A device for assisting in navigation during the placement of surgical hardware comprising:
    a first rail running parallel to a longitudinal axis, the first rail including a first track along an upper surface, the first track having spacing blocks and a plurality of openings configured to accept at least one guide block;

a second rail, offset from the first rail, running parallel to the longitudinal axis; and a central crossbar running between the first rail and the second rail, the central crossbar running parallel to a transverse axis.

2. The device of claim 1 wherein the second rail has a second track along an upper surface, the second track having spacing blocks and a plurality of openings configured to accept at least one guide block.

3. The device of claim 1 further comprising a first bubble level attached to the first rail, the first bubble level displaying indicia of whether the longitudinal axis is level to the ground.

4. The device of claim 3 further comprising a second bubble level attached to the second rail, the second bubble level displaying indicia of whether the transverse axis is level to the ground.

5. The device of claim 1 wherein the first rail has a plurality of lower slide slots configured to couple with at least one stacking support to orient the device with the respect to the ground.

6. The device of claim 1 wherein:

the central crossbar includes a first radiodense metal strip on an upper surface; and a second radiodense metal strip is included on one of the following: a side surface of first rail; or a side surface of the second rail.

7. The device of claim 6 wherein the first metal strip and the second metal strip are each substantially 50 mm in length.

\* \* \* \* \*